United States Patent [19]
Gericke et al.

[11] Patent Number: 5,807,896
[45] Date of Patent: Sep. 15, 1998

[54] ARYLBENZOYLGUANIDINES

[75] Inventors: Rolf Gericke, Seeheim; Dieter Dorsch, Ober-Ramstadt; Manfred Baumgarth, Darmstadt; Klaus-Otto Minck, Ober-Ramstadt; Norbert Beier, Reinheim, all of Germany

[73] Assignee: Merck Patent Gesellschaft mit Beschrankter Hafting, Germany

[21] Appl. No.: 519,182

[22] Filed: Aug. 25, 1995

[30] Foreign Application Priority Data

Aug. 28, 1994 [DE] Germany .................. 44 30 213.4

[51] Int. Cl.$^6$ ............ A61K 31/165; C07C 279/22; C07C 277/08
[52] U.S. Cl. ............ 514/18; 514/617; 564/162; 564/237
[58] Field of Search .................. 564/162, 237; 514/618, 617

[56] References Cited

U.S. PATENT DOCUMENTS 5,516,805   5/1996   Lang et al. .................. 514/620

FOREIGN PATENT DOCUMENTS 2099445   1/1994   Canada .
43 18 756   12/1994   Germany .

*Primary Examiner*—Allen J. Robinson
*Assistant Examiner*—Barbara Badio
*Attorney, Agent, or Firm*—Millen, White, Zelano & Branigan, P.C.

[57] ABSTRACT

Arylbenzoylguanidines of the formula I

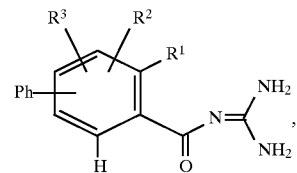

in which $R^1$, $R^2$, $R^3$ and Ph have the given meanings herein, and also the physiologically harmless salts thereof, exhibit antiarrhythmic properties and act as inhibitors of the cellular $Na^+/H^+$ antiporter.

7 Claims, No Drawings

ARYLBENZOYLGUANIDINES

The invention relates to ortho-substituted arylbenzoylguanidines of the formula I

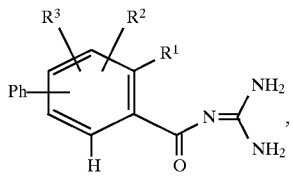

in which $R^1$ is A, $CF_3$, $CH_2F$, $CHF_2$, $C_2F_5$, CN, $NO_2$, Hal, C≡CH or —X—$R^4$, $R^2$ and $R^3$ are, in each case independently of each other, H, Hal, A, —X—$R^4$, CN, $NO_2$, $CF_3$, $CH_2F$, $CHF_2$, $C_2F_5$, $CH_2CF_3$, —$SO_n$—$R^6$, —$SO_2NR^4R^5$, Ph or OPh, $R^4$ is H, A, cycloalkyl having from 5 to 7 C atoms, cycloalkylmethyl having from 6 to 8 C atoms, $CF_3$, $CH_2F$, $CHF_2$, $CH_2CF_3$, Ph or —$CH_2$-Ph, $R^5$ is H or A, or else $R^4$ and $R^5$ are together alkylene having from 4 to 5 C atoms, where one $CH_2$ group can also be replaced by O, S, NH, N-A or N—$CH_2$-Ph, $R^6$ is A or Ph, A is alkyl having from 1 to 6 C atoms, X is O, S or $NR^5$, Ph is phenyl, naphthyl or biphenylyl which is unsubstituted or is substituted once, twice or three times by A, OA, $NR^4R^5$, F, Cl, Br, I or $CF_3$, n is 1 or 2, and Hal is F, Cl, Br or I, and the physiologically harmless salts thereof.

The object of the invention was to discover novel compounds having valuable properties, in particular those compounds which can be used for preparing medicaments.

It was found that the compounds of the formula I, and their physiologically harmless salts, possess valuable pharmacological properties while being well tolerated.

The novel compounds are inhibitors of the cellular $Na^+/H^+$ antiporter, i.e. active compounds which inhibit the cellular $Na^+/H^+$ exchange mechanism (Düsing et al., Med. Klin. 87, 378–384 (1992)), and thus represent good antiarrhythmic agents which are particularly suitable for treating arrhythmias which arise as a result of lack of oxygen.

The active compound of the acylguanidine group which is most well known is amiloride. However, this substance first and foremost exhibits hypotensive and saluretic effects, which are undesirable when treating disturbances of cardiac rhythm, in particular, whereas the antiarrhythmic properties are only very weakly expressed.

In addition to this, EP 04 16 499, for example, discloses compounds which are structurally similar.

The invention relates to compounds of the formula I and their pharmaceutically acceptable salts.

The novel substances of the present application exhibit a good cardioprotective effect and are therefore particularly suitable for the treatment of infarction, for infarction prophylaxis and for treating angina pectoris. In addition, the substances counteract all types of pathological hypoxic and ischaemic damage, so that the disorders which are caused primarily or secondarily by such damage can be treated. The active compounds are also well suited for preventive applications.

Because of the protective effects of these substances in pathological hypoxic or ischaemic situations, there are further possibilities for using these compounds in association with surgical interventions, for protecting organs which are from time to time less well supplied, in association with organ transplantations, for protecting the organs which are being removed, in association with angioplastic blood vessel or cardiac surgery, in association with ischaemias of the nervous system, in association with the therapy of conditions of shock, and for prophylactic prevention of essential hypertension.

In addition, the compounds can also be employed as therapeutic agents in diseases arising from cell proliferation, such as arteriosclerosis, late complications in diabetes, tumour diseases, fibrotic diseases, in particular of the lung, liver and kidneys, and also organ hypertrophies and hyperplasias. In addition to this, these substances are also suitable for being used diagnostically for diagnosing diseases which are associated with an increased activity of the $Na^+/H^+$ antiporter, e.g. in erythrocytes, thrombocytes or leucocytes.

The effects of the compounds can be ascertained using methods which are known per se, as described, for example, by N. Escobales and J. Figueroa in J. Membrane Biol. 120, 41–49 (1991) or by L. Counillon, W. Scholz, H. J. Lang and J. Pouysségur in Mol. Pharmacol. 44, 1041–1045 (1993).

Examples of suitable experimental animals are mice, rats, guinea pigs, dogs, cats, monkeys or pigs.

The compounds may, therefore, be used as pharmaceutical active compounds in human and veterinary medicine. In addition, they can be used as intermediates for preparing further pharmaceutical active compounds.

In the given formulae, A is preferably a branched or unbranched alkyl group having 1–6, preferably 1–4, in particular 1, 2 or 3, C atoms, specifically methyl for preference, with ethyl, propyl, isopropyl, butyl or isobutyl also being preferred and sec-butyl, tert-butyl, pentyl, isopentyl (3-methylbutyl), hexyl or isohexyl (4-methylpentyl) furthermore being preferred.

$R^1$ is preferably A, OA or Hal, in particular Br or Cl, and also, in addition, preferably $CH_2F$, $CHF_2$, $CF_3$ or $C_2F_5$.

$R^2$ and $R^3$ are preferably, independently of each other, H, A-$SO_2$, A, $CF_3$, Cl, Br, CN or OA. Particularly preferably, one of the two radicals is $H_3C$—$SO_2$— while the other is preferably hydrogen. If one of the radicals is A-$SO_2$—, the latter is then preferably in the meta position to the guanidinocarbonyl group. A benzoyl group which has a methylsulfonyl radical in the 5 position and an alkyl group, preferably methyl or ethyl, in the 2 position is also particularly preferred.

$R^4$ is preferably H or A, as is $R^5$.

If $R^4$ and $R^5$ are together alkylene, the alkylene group is then preferably unbranched, specifically —$(CH_2)_k$— for preference, where k is 4 or 5; however, —$(CH_2)_2$—O—$(CH_2)_2$—, —$(CH_2)_2$—NH—$(CH_2)_2$—, —$(CH_2)_2$—NA-$(CH_2)_2$—, —$CH_2$—O—$(CH_2)_2$—, —$CH_2$—NH—$(CH_2)_2$—, or —$CH_2$—NA-$(CH_2)_2$— or —CO—$(CH_2)_3$—, —CO—$(CH_2)_4$— or —$CH_2$—CO—$(CH_2)_2$ are also preferred.

Ph is preferably phenyl which is unsubstituted or substituted once by Cl, Br, A, OA, $NH_2$, NHA, $NA_2$ or $CF_3$.

$R^6$ is preferably A, in particular methyl, or else preferably also unsubstituted phenyl.

The radical X is preferably O or NH.

It applies generally that all the radicals, such as $R^4$, $R^5$ or Ph, which occur several times can be identical or different, i.e. are independent of each other.

Accordingly, the invention relates, in particular, to those compounds of the formula I in which at least one of the said radicals has one of the abovementioned, preferred meanings. Some preferred groups of compounds can be expressed by the following formulae Ia to Ih, which conform to the formula I and in which the radicals which are not more precisely described have the meaning given in association with formula I, in which, however, in Ia $R^1$ is A and $R^2$ is —$SO_2$—$CH_3$ or —$SO_2$—$NH_2$;

in Ib $R^1$ is A and Ph is phenyl which is unsubstituted or is substituted once by A or Hal;

in Ic $R^1$ is A and $R^2$ is $SO_2$—$CH_3$;

in Id Ph is in the para position with respect to the guanidinocarbonyl group and is phenyl which is unsubstituted or which is substituted once by A;

in Ie Ph has the preferred meaning which is mentioned under Id, and $R^2$ is $SO_2$-A and is located in the meta position with respect to the guanidinocarbonyl group;

in If $R^1$ is methyl, ethyl or else propyl or isopropyl, and $R^3$ is H;

in Ig the radical Ph is located in the p position with respect to the guanidinocarbonyl group, $R^2$ is $SO_2$—$CH_3$ and $R^3$ is H;

in Ih $R^1$ is Hal and $R^2$ is $SO_2$-A.

The invention also relates to a process for preparing the compounds of the abovementioned formula I, and also the salts thereof, characterized in that a compound of the formula II

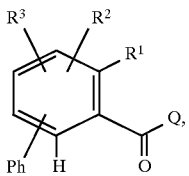

in which $R^1$, $R^2$, $R^3$ and Ph have the previously mentioned meanings, and

Q is Cl, Br, OA, O—CO-A, O—CO-Ph or OH, or another reactive, esterified OH group or leaving group which can readily be substituted nucleophilically, is reacted with guanidine, or in that a benzoylguanidine of the formula III

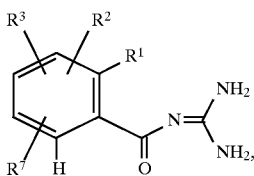

in which $R^1$, $R^2$ and $R^3$ have the previously mentioned meanings, and $R^7$ is Cl, Br, I or O—$SO_2$—$R^8$, and $R^8$ is A, Ph or $CF_3$, is reacted with a compound of the formula IV

in which $R^9$ is in each case H, A or, together, alkylene having from 2 to 4 C atoms, or in that a compound which contains one or more reducible group(s) and/or one or more additional C—C and/or C—N bond(s) in place of one or more hydrogen atoms, but which otherwise conforms to the formula I, is treated with a reducing agent, or in that a compound which contains one or more solvolysable group(s) in place of one or more hydrogen atoms, but which otherwise conforms to the formula I, is treated with a solvolysing agent, and/or in that a base of the formula I which has been obtained is converted into one of its salts by being treated with an acid.

The compounds of the formula I are otherwise prepared by methods which are known per se, as described in the literature (e.g. in the standard works such as Houben-Weyl, Methoden der organischen Chemie (Methods of organic chemistry), Georg-Thieme-Verlag, Stuttgart; Organic Reactions, John Wiley & Sons, Inc., New York; and also in the abovementioned patent application EP 0416499), and specifically under reaction conditions which are known for the said reactions and which are suitable for these reactions. In this context, use can also be made of variants which are known per se but which have not been mentioned in any detail here.

If desired, the starting compounds may also be formed in situ, such that they are not isolated from the reaction mixture but are instead immediately subjected to further reaction to form the compounds of the formula I.

Preferably, compounds of the formula I are prepared by reacting an activated carboxylic acid derivative of the formula II, where Q is particularly preferably Cl or —O—$CH_3$, with guanidine. Reaction variants are particularly suitable in which the free carboxylic acid II (Q=OH) is converted, in a manner known per se, into the particular activated derivative and the latter is then directly, without intermediate isolation, reacted with guanidine. Examples of methods in which intermediate isolation can be dispensed with are activation with carbonyldiimidazole or dicyclohexylcarbodiimide or the Mukayama variant (Angew. Chem. 91, 788–812 (1979)).

As a rule, the carboxylic acids of the formula II are known. They are prepared, in particular, by means of Pd-catalyzed crosscoupling, such as, for example, the Suzuki coupling (Synlett. 207, 1992). Examples of preferred catalysts are $Pd(PPh_3)_4$ or $(Ph_3P)_2PdCl_2$.

The carboxylic acids of the formula II are also prepared by nucleophilic aromatic substitution, proceeding from suitable benzoic acid derivatives, by reaction with corresponding arylboronic acids or esters of the formula IV. The reaction is effected in analogy with the reaction of the compounds III and IV. It is described below.

Examples of particularly suitable compounds of the formula IV are phenylboronic acid and the 2-, 3- or 4-alkylphenylboronic acids or their alkyl esters, which, where appropriate, can possess additional substituents.

The reaction of a reactive carboxylic acid derivative of the formula II with guanidine is effected in a manner known per se, preferably in a protic or aprotic, polar or non-polar, inert organic solvent.

Suitable solvents for the reaction of the compounds III and IV are mentioned below. However, particularly preferred solvents are methanol, THF, dimethoxyethane, dioxane or mixtures prepared therefrom, and also water. Temperatures of between 20° and the boiling point of the solvent, for example, are suitable as the reaction temperature. The reaction times are between 5 min. and 12 hrs. It is expedient to include an acid-capturing agent in the reaction. Any type of base which does not interfere with the reaction itself is suitable for this purpose. However, the use of inorganic bases, such as potassium carbonate, or of organic bases, such as triethylamine or pyridine, or else an excess of the guanidine, is particularly suitable.

Compounds of the formula I according to claim 1 can also be prepared by reacting a benzoylguanidine of the formula III with a compound of the formula IV. The starting compounds of the formula III can be prepared, in a simple manner, by reacting appropriately substituted benzoic acids, or reactive acid derivatives, such as, for example, acid halides, esters or anhydrides, which can be derived therefrom, with guanidine under reaction conditions which are known per se for amide preparation and which are generally customary. Particularly suitable reaction variants are again those indicated previously for the reaction of compound II with guanidine.

The compounds of the formula IV are known per se, as are the methods for preparing them. If they are not known, they can be prepared by the methods which are known per se.

The preparation of the compound II, and also the reaction of the compound III with a compound of the formula IV, are effected in a manner known per se, preferably in a protic or aprotic, polar, inert organic solvent.

In the preparation of II, in the reaction of II with guanidine or in the reaction of III with IV, it is likewise expedient to carry out the reaction in the presence of a base or with an excess of the basic component. Preferred examples of suitable bases are alkali metal or alkaline earth metal hydroxides, carbonates or alcoholates, or organic bases such as triethylamine or pyridine, which can also be used in excess and which can then simultaneously serve as solvent.

Suitable inert solvents are, in particular, alcohols, such as methanol, ethanol, isopropanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol) or ethylene glycol dimethyl ether (diglyme); ketones, such as acetone or butanone; nitriles, such as acetonitrile; nitro compounds, such as nitromethane or nitrobenzene; esters, such as ethyl acetate or hexamethylphosphoric triamide; sulphoxides, such as dimethyl sulphoxide (DMSO); chlorinated hydrocarbons, such as dichloromethane, chloroform, trichloroethylene, 1,2-dichloroethane or carbon tetrachloride; hydrocarbons, such as benzene, toluene or xylene. In addition to this, mixtures of these solvents with each other are also suitable.

A particularly preferred approach when reacting III with IV consists of suspending the appropriate benzoylguanidine in an inert solvent, such as toluene, then treating it with tetrakis-(triphenylphosphine)palladium(0) and subsequently adding the desired boronic acid, or an appropriate boronic ester, dropwise (Suzuki coupling).

The compounds of formula I can also be obtained by liberating them from their functional derivatives by means of solvolysis, in particular hydrolysis, or by means of hydrogenolysis.

Starting compounds which are preferred for the solvolysis or hydrogenolysis are those which, while otherwise conforming to the formula I, contain corresponding protected amino and/or hydroxyl groups in place of one or more free amino and/or hydroxyl groups, preferably those which carry an amino protective group in place of an H atom which is bonded to an N atom, in particular those which carry an R'—N group, in which R' is an amino protective group, in place of a HN group, and/or those which carry a hydroxyl protective group in place of the H atom of a hydroxyl group, for example those which, while conforming to the formula I, carry an OR" group, in which R" is a hydroxyl protective group, in place of an OH group.

Several—identical or different—protected amino and/or hydroxyl groups can also be present in the molecule of the starting compound. If the protective groups which are present differ from each other, they can then, in many cases, be eliminated selectively.

The expression "amino protective group" is well known and refers to groups which are suitable for protecting (for blocking) an amino group against chemical reactions and which can readily be removed once the desired chemical reaction has been carried out at another site in the molecule. Typical examples of such groups are, in particular, unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl or triphenylmethyl). Since the amino protective groups are removed following the desired reaction (or sequence of reactions), their nature and size is otherwise not critical; nevertheless, those are preferred which have 1–20, in particular 1–8, C atoms. In connection with the present process, the expression "acyl group" is to be interpreted in its widest sense. It encompasses acyl groups which are derived from aliphatic, araliphatic, aromatic or heterocyclic carboxylic acids or sulfonic acids, as well as, in particular, alkoxycarbonyl, aryloxycarbonyl and, especially, aralkoxycarbonyl groups. Examples of acyl groups of this nature are alkanoyl, such as acetyl, propionyl or butyryl; aralkanoyl, such as phenylacetyl; aroyl, such as benzoyl or toluoyl; aryloxyalkanoyl, such as phenoxyacetyl; alkoxycarbonyl, such as methoxycarbonyl, ethoxycarbonyl, 2,2,2-trichloroethoxycarbonyl, isopropoxycarbonyl, tert-butoxycarbonyl (BOC) or 2-iodoethoxycarbonyl; aralkyloxycarbonyl, such as benzyloxycarbonyl (CBZ), 4-methoxybenzyloxycarbonyl or 9-fluorenylmethoxycarbonyl (FMOC). Preferred amino protective groups are BOC, DNP and BOM and, in addition, CBZ, benzyl and acetyl.

The expression "hydroxyl protective group" is likewise well known and refers to groups which are suitable for protecting a hydroxyl group against chemical reactions and which can readily be removed once the desired chemical reaction has been carried out at another site in the molecule. The abovementioned unsubstituted or substituted aryl, aralkyl or acyl groups, and also alkyl groups, are typical examples of such groups. The nature and size of the hydroxyl protective groups are not critical since the groups are removed once again following the desired chemical reaction or sequence of reactions; groups having 1–20, in particular 1–10, C atoms are preferred. Some examples of hydroxyl protective groups are tert-butyl, benzyl, p-nitrobenzoyl, p-toluenesulphonyl and acetyl, with benzyl and acetyl being particularly preferred.

The functional derivatives of the compounds of the formula I which are to be used as starting compounds can be prepared using customary methods as described, for example, in the specified standard works and patent applications, for example by reacting compounds which conform to the formulae II and III, with, however, at least one of these compounds containing a protective group in place of a H atom.

Depending on the protective group employed, the compounds of the formula I are liberated from their functional derivatives using, for example, strong acids, expediently using trifluoroacetic acid or perchloric acid, or else using other strong inorganic acids, such as hydrochloric acid or sulphuric acid, or strong organic carboxylic acids, such as trichloroacetic acid, or sulphonic acids, such as benzenesulphonic acid or p-toluenesulphonic acid. While it is possible to carry out the reaction in the presence of an additional inert solvent, this is not always necessary.

Those solvents which are preferably used as inert solvents are organic, for example carboxylic acids, such as acetic acid, ethers, such as tetrahydrofuran (THF) or dioxane, amides, such as dimethylformamide (DMF), halogenated hydrocarbons, such as dichloromethane, and also, in addition, alcohols, such as methanol, ethanol or isopropanol, and also water. Mixtures of the abovementioned solvents are also suitable. Trifluoroacetic acid is preferably used in excess without adding any further solvent; perchloric acid is used in the form of a mixture consisting of acetic acid and 70% perchloric acid in a ratio of 9:1. The reaction temperatures for the cleavage are expediently between about 0° and about 50°; the reaction is preferably carried out at between 15° and 30° (room temperature).

The BOC group can preferably, for example, be eliminated using 40% trifluoroacetic acid in dichloro-methane or using from about 3 to 5N HCl in dioxane at 15°–60°; the FMOC group can be eliminated using an approximately 5–20% solution of dimethylamine, diethylamine or piperidine in DMF at 15°–50°. The DNP group is also successfully eliminated, for example, using an approximately 3–10% solution of 2-mercaptoethanol in DMF/water at 15°–30°.

Protective groups (e.g. BOM, CBZ or benzyl) which can be removed hydrogenolytically can, for example, be eliminated by being treated with hydrogen in the presence of a catalyst (e.g. a precious metal catalyst such as palladium, expediently on a support such as carbon). The solvents mentioned above, in particular, for example, alcohols, such as methanol or ethanol, or amides, such as DMF, are suitable for use in this context. As a rule, the hydrogenolysis is carried out at temperatures of between about 0° and 100° and at pressures of between about 1 and 200 bar, preferably at 20°–30° and at 1–10 bar. The CBZ group is successfully hydrogenolyzed, for example, on 5–10% Pd—C in methanol at 20°–30°.

A base of the formula I can also be converted into the affiliated acid addition salt using an acid. Acids which are suitable for this reaction are those which give rise to physiologically harmless salts. Thus, use can be made of inorganic acids, for example sulphuric acid, nitric acid, hydrohalic acids, such as hydrochloric acid or hydrobromic acid, phosphoric acids, such as orthophosphoric acid, or sulphamic acid, and also of organic acids, in particular aliphatic, alicyclic, araliphatic, aromatic or heterocyclic monobasic or polybasic carboxylic acids, sulphonic acids or sulphuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulphonic acid, ethanesulphonic acid, ethanedisulphonic acid, 2-hydroxyethanesulphonic acid, benzenesulphonic acid, p-toluenesulphonic acid, naphthalene monosulphonic and disulphonic acids or laurylsulphuric acid The compounds of the formula I and their physiologically harmless salts may be used to produce pharmaceutical preparations, especially by a non-chemical route such as mechanical mixing. When being used for this purpose, they can be brought, together with at least one solid, liquid and/or semiliquid carrier substance or auxiliary substance and, where appropriate, in combination with one or more additional active compound(s), into a suitable dosage form.

The invention furthermore relates to compositions, in particular pharmaceutical preparations, which contain at least one compound of the formula I and/or one of its physiologically harmless salts.

These preparations can be used as medicaments in human or veterinary medicine. Suitable carrier substances are organic or inorganic substances which are suitable for enteral (e.g. oral), parenteral or topical administration and which do not react with the novel compounds, for example water, vegetable oils, benzyl alcohols, polyethylene glycols, glycerol triacetate, gelatin, carbohydrates, such as lactose or starch, magnesium stearate, talc, lanolin or vaseline. For oral applications, use is made, in particular, of tablets, coated tablets, capsules, syrups, juices or drops, for rectal application of suppositories, for parenteral application of solutions, preferably oily or aqueous solutions, and also of suspensions, emulsions or implants, and for topical application of ointments, creams, pastes, lotions, gels, sprays, foams, aerosols, solutions (e.g. solutions in alcohols, such as ethanol or isopropanol, acetonitrile, DMF, dimethylacetamide or 1,2-propanediol, or their mixtures with each other and/or with water) or powders. The novel compounds can also be lyophilized and the resulting lyophilisates used, for example, to produce preparations for injection.

Liposomal preparations are also especially suitable for topical applications. The given preparations can be sterilized and/or contain auxiliary substances such as glidants, preservatives, stabilizers and/or wetting agents, emulsifiers, salts for influencing the osmotic pressure, buffering substances, colouring substances, flavouring substances and/or aromatizing substances. They can, if desired, also contain one or more additional active compounds, e.g. one or more vitamins.

The compounds of the formula I, and their physiologically harmless salts, can be administered to humans or animals, in particular mammals such as monkeys, dogs, cats, rats or mice, and be used for the therapeutic treatment of the human or animal body and also for controlling diseases, in particular in association with the therapy and/or prophylaxis of disturbances of the cardiovascular system. They are suitable, therefore, for treating arrhythmias, in particular when the latter are caused by a lack of oxygen, angina pectoris, infarctions, ischaemias of the nervous system, such as, for example, stroke or cerebral oedemas, and conditions of shock, and also for preventive treatment.

The substances can also be employed as therapeutic agents in diseases in which cell proliferation plays a role, such as arteriosclerosis, late complications in diabetes, tumour diseases, fibroses and organ hypertrophies and hyperplasias.

In this context, the substances according to the invention are as a rule administered in analogy with known antiarrhythmics, e.g. aprindine, preferably in doses of between about 0.01 and 5 mg, in particular of between 0.02 and 0.5 mg per dosage unit. The daily dose is preferably between about 0.0001 and. 0.1, in particular between 0.0003 and 0.01, mg/kg of body weight. However, the special dose for each particular patient depends on a wide variety of factors, for example on the activity of the special compound employed, on the age, on the body weight, on the general state of health, on the sex, on the diet, on the time and route of administration, on the speed of excretion, on the combination of medicines being employed, and on the severity of the particular disease to which the therapy applies. oral administration is preferred. The "physiologically harmless salts" include "pharmaceutically acceptable salts".

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application German application number P 44 30 213.4, are hereby incorporated by reference.

In the examples which follow, "customary working-up" denotes:

If required, water is added and extraction takes place using an organic solvent such as ethyl acetate; the organic phase is separated off and dried over sodium sulphate, after which it is filtered and evaporated; the residue is purified by chromatography and/or crystallization.

EXAMPLE 1

A solution of 1.8 g of methyl 2-methyl-4-(4-methylphenyl) -5-methylsulphonylbenzoate [obtainable by reacting methyl 3-methylsulphonyl-4-bromo-6-methylbenzoate with tolylboronic acid] and 1.5 g of guanidine in 50 ml of methanol is boiled for five hours and the solvent is then removed. The residue is treated with water and the crop of crystals which remains is filtered off with suction and treated with dilute sodium hydroxide solution. The solid residue is filtered off and recrystallized from ethanol, and N-diaminomethylene-2-methyl-4-(4-methylphenyl)-5-methylsulphonylbenzamide is obtained, m.p. 222°–224°.

The following are obtained in an analogous manner by reacting guanidine with methyl 2-ethyl-4-(4-methylphenyl)-5-methylsulphonylbenzoate, N-diaminomethylene-2-ethyl-4-(4-methylphenyl)-5-methylsulphonylbenzamide;
with methyl 2-propyl-4-(4-methylphenyl)-5-methylsulphonylbenzoate, N-diaminomethylene-2-propyl-4-(4-methylphenyl)-5-methylsulphonylbenzamide;
with methyl 2-isopropyl-4-(4-methylphenyl)-5-methylsulphonylbenzoate, N-diaminomethylene-2-isopropyl-4-(4-methylphenyl)-5-methylsulphonylbenzamide;
with methyl 2-butyl-4-(4-methylphenyl)-5-methylsulphonylbenzoate, N-diaminomethylene-2-butyl-4-(4-methylphenyl)-5-methylsulphonylbenzamide;
with methyl 2-(2-butyl)-4-(4-methylphenyl)-5-methylsulphonylbenzoate, N-diaminomethylene-2-(2-butyl)-4-(4-methylphenyl)-5-methylsulphonylbenzamide;
with methyl 2-methyl-4-phenyl-5-methylsulphonylbenzoate, N-diaminomethylene-2-methyl-4-phenyl-5-methylsulphonylbenzamide;
with methyl 2-ethyl-4-phenyl-5-methylsulphonylbenzoate, N-diaminomethylene-2-ethyl-4-phenyl-5-methylsulphonylbenzamide;
with methyl 2-propyl-4-phenyl-5-methylsulphonylbenzoate, N-diaminomethylene-2-propyl-4-phenyl-5-methylsulphonylbenzamide;
with methyl 2-isopropyl-4-phenyl-5-methylsulphonylbenzoate, N-diaminomethylene-2-isopropyl-4-phenyl-5-methylsulphonylbenzamide;
with methyl 2-butyl-4-phenyl-5-methylsulphonylbenzoate, N-diaminomethylene-2-butyl-4-phenyl-5-methylsulphonylbenzamide;
with methyl 2-(2-butyl)-4-phenyl-5-methylsulphonylbenzoate, N-diaminomethylene-2-(2-butyl)-4-phenyl-5-methylsulphonylbenzamide;
with methyl 2-ethyl-4-(3-methylphenyl)-5-methylsulphonylbenzoate, N-diaminomethylene-2-ethyl-4-(3-methylphenyl)-5-methylsulphonylbenzamide;
with methyl 2-chloro-4-(4-methylphenyl)-5-methylsulphonylbenzoate, N-diaminomethylene-2-chloro-4-(4-methylphenyl)-5-methylsulphonylbenzamide;
with methyl 2-bromo-4-(4-methylphenyl)-5-methylsulphonylbenzoate, N-diaminomethylene-2-bromo-4-(4-methylphenyl)-5-methylsulphonylbenzamide;
with methyl 2-fluoromethyl-4-(4-methylphenyl)-5-methylsulphonylbenzoate, N-diaminomethylene-2-fluoromethyl-4-(4-methylphenyl)-5-methylsulphonylbenzamide;
with methyl 2-trifluoromethyl-4-(4-methylphenyl)-5-methylsulphonylbenzoate, N-diaminomethylene-2-trifluoromethyl-4-(4-methylphenyl)-5-methylsulphonylbenzamide;
with methyl 2-pentafluoroethyl-4-(4-methylphenyl)-5-methylsulphonylbenzoate, N-diaminomethylene-2-pentafluoroethyl-4-(4-methylphenyl)-5-methylsulphonylbenzamide;
with methyl 2-methoxy-4-(4-methylphenyl)-5-methylsulphonylbenzoate, N-diaminomethylene-2-methoxy-4-(4-methylphenyl)-5-methylsulphonylbenzamide;
with methyl 2-cyano-4-(4-methylphenyl)-5-methylsulphonylbenzoate, N-diaminomethylene-2-cyano-4-(4-methylphenyl)-5-methylsulphonylbenzamide;
with methyl 2-nitro-4-(4-methylphenyl)-5-methylsulphonylbenzoate, N-diaminomethylene-2-nitro-4-(4-methylphenyl)-5-methylsulphonylbenzamide;
with methyl 2-ethynyl-4-(4-methylphenyl)-5-methylsulphonylbenzoate, N-diaminomethylene-2-ethynyl-4-(4-methylphenyl)-5-methylsulphonylbenzamide.

EXAMPLE 2

700 mg of N-diaminomethylene-2-methyl-4-(4-methylphenyl)-5-methylsulphonylbenzamide [obtainable in accordance with Ex. 1] are suspended in 50 ml of water, and 1.8 ml of 1N HCl are added to this suspension while stirring. Following filtration and lyophilization, N-diaminomethylene-2-methyl-4-(4 -methylphenyl)-5-methylsulphonylbenzamide, hydrochloride, is obtained, m.p. 205°.

The following hydrochlorides are obtained from the free bases in an analogous manner:

N-diaminomethylene-2-ethyl-4-(4-methylphenyl)-5-methylsulphonylbenzamide, hydrochloride;
N-diaminomethylene-2-propyl-4-(4-methylphenyl)-5-methylsulphonylbenzamide, hydrochloride;
N-diaminomethylene-2-isopropyl-4-(4-methylphenyl)-5-methylsulphonylbenzamide, hydrochloride;
N-diaminomethylene-2-butyl-4-(4-methylphenyl)-5-methylsulphonylbenzamide, hydrochloride;
N-diaminomethylene-2-(2-butyl)-4-(4-methylphenyl)-5-methylsulphonylbenzamide, hydrochloride;
N-diaminomethylene-2-ethyl-4-phenyl-5-methylsulphonylbenzamide, hydrochloride;
N-diaminomethylene-2-propyl-4-phenyl-5-methylsulphonylbenzamide, hydrochloride;
N-diaminomethylene-2-isopropyl-4-phenyl-5-methylsulphonylbenzamide, hydrochloride;

N-diaminomethylene-2-butyl-4-phenyl-5-methylsulphonylbenzamide, hydrochloride;
N-diaminomethylene-2-(2-butyl)-4-phenyl-5-methylsulphonylbenzamide, hydrochloride;
N-diaminomethylene-2-methyl-4-phenyl-5-methylsulphonylbenzamide, hydrochloride;
N-diaminomethylene-2-chloro-4-(4-methylphenyl)-5-methylsulphonylbenzamide, hydrochloride;
N-diaminomethylene-2-bromo-4-(4-methylphenyl)-5-methylsulphonylbenzamide, hydrochloride;
N-diaminomethylene-2-fluoromethyl-4-(4-methylphenyl)-5-methylsulphonylbenzamide, hydrochloride;
N-diaminomethylene-2-trifluoromethyl-4-(4-methylphenyl)-5-methylsulphonylbenzamide, hydrochloride;
N-diaminomethylene-2-pentafluoroethyl-4-(4-methylphenyl)-5-methylsulphonylbenzamide, hydrochloride;
N-diaminomethylene-2-methoxy-4-(4-methylphenyl)-5-methylsulphonylbenzamide, hydrochloride;
N-diaminomethylene-2-cyano-4-(4-methylphenyl)-5-methylsulphonylbenzamide, hydrochloride;
N-diaminomethylene-2-nitro-4-(4-methylphenyl)-5-methylsulphonylbenzamide, hydrochloride;
N-diaminomethylene-2-ethynyl-4-(4-methylphenyl)-5-methylsulphonylbenzamide, hydrochloride.

EXAMPLE 3

10 mg of tetrakis(triphenylphosphine)-Pd(0) and 1.8 g of $Na_2CO_3$, dissolved in 15 ml of water, are added in succession to a suspension of 6.02 g of N-diaminomethylene-2-methyl-4-bromo-5-methylsulphonylbenzamide [obtainable by reacting 2-methyl-4-bromo-5-methylsulphonylbenzoyl chloride with guanidine in the presence of triethylamine] in 100 ml of toluene, and the reaction mixture is warmed to 50°–60°. 3 g of 3-methylphenylboronic acid, dissolved in 20 ml of ethanol, are then added dropwise, and the mixture is stirred at 90° for 2 h. Following filtration, removal of the solvent and customary working-up, N-diaminomethylene-2-methyl-4-(3-methylphenyl)-5-methylsulphonylbenzamide is obtained, from which the corresponding hydrochloride or methanesulfonate is obtained after treatment with a dilute, aqueous solution of HCl methanesulfonic acid and freeze-drying.

The following are obtained in an analogous manner by reacting N-diaminomethylene-2-methyl-4-bromo-5-methylsulphonylbenzamide with 2,4-dimethylphenylboronic acid, N-diaminomethylene-2-methyl-4-(2,4-dimethylphenyl)-5-methylsulphonylbenzamide, hydrochloride;
with 2,4-dichlorophenylboronic acid, N-diaminomethylene-2-methyl-4-(2,4-dichlorophenyl)-5-methylsulphonylbenzamide, hydrochloride, m.p. 209°–211°;
with 4-methoxyphenylboronic acid, N-diaminomethylene-2-methyl-4-(4-methoxyphenyl)-5-methylsulphonylbenzamide, hydrochloride;
with 4-fluorophenylboronic acid, N-diaminomethylene-2-methyl-4-(4-fluorophenyl)-5-methylsulphonylbenzamide, m.p. 235°–237°, methanesulfonate m.p. 191°–194°;
with 3,5-bis-(tri fluoromethylphenyl)boronic acid, N-diaminomethylene-2-methyl-4-[3,5-bis-(tri fluoromethylphenyl)]-5-methylsulphonylbenzamide, m.p. 190°–194°, methanesulfonate 150°;
with 3-bromophenylboronic acid, N-diaminomethylene-2-methyl-4-(3-bromophenyl)-5-methylsulphonylbenzamide, hydrochloride;
with 2,4-dimethoxyphenylboronic acid, N-diaminomethylene-2-methyl-4-(2,4-dimethoxyphyenyl)-5-methylsulphonylbenzamide, hydrochloride;
with 3,5-dichlorophenylboronic acid, N-diaminomethylene-2-methyl-4-(3,5-dichlorophenyl)-5-methylsulphonylbenzamide, m.p. 215°–218°, methanesulfonate 231°–233°.

EXAMPLE 4

1.0 g of 2-ethyl-3-methylsulphonyl-4-phenylbenzoic acid [obtainable by reacting methyl 2-ethyl-3-methylsulphonyl-4-bromobenzoate with phenylboronic acid in the presence of tetrakis(triphenylphosphine)-Pd(0) and then hydrolyzing] is dissolved in 15 ml of 1-methylpyrrolidone, and 0.67 g of 1-methyl-2-chloropyridinium chloride is added to this solution which is then stirred for 15 min. 0.9 g of guanidinium chloride and 2.6 ml of diisopropylethylamine are then added, and the mixture is stirred at room temperature for one hour. N-Diaminomethylene-2-ethyl-3-methylsulphonyl-4-phenylbenzamide is obtained after customary working-up.

The following are obtained in an analogous manner from 2-methyl-3-methylsulphonyl-4-(3-chlorophenyl)-benzoic acid, N-diaminomethylene-2-methyl-3-methylsulphonyl-4-(3-chlorophenyl)benzamide;
from 2-nitro-3-methylsulphonyl-4-(4-methoxyphenyl)-benzoic ester, N-diaminomethylene-2-nitro-3-methylsulphonyl-4-(4-methoxyphenyl)benzamide;
from 2-cyano-3-methylsulphonyl-4-phenylbenzoic acid, N-diaminomethylene-2-cyano-3-methylsulphonyl-4-phenylbenzamide;
from 2-ethynyl-3-methylsulphonyl-4-(4-chlorophenyl)-benzoic acid, N-diaminomethylene-2-ethynyl-3-methylsulphonyl-4-(4-chlorophenyl)benzamide;
from 2-fluoro-3-methylsulphonyl-4-phenylbenzoic acid, N-diaminomethylene-2-fluoro-3-methylsulphonyl-4-phenylbenzamide;
from 2-difluoromethyl-3-methylsulphonyl-4-phenylbenzoic acid, N-diaminomethylene-2-difluoromethyl-3-methylsulphonyl-4-phenylbenzamide;
from 2-fluoromethyl-3-methylsulphonyl-4-(4-methylphenyl)benzoic acid, N-diaminomethylene-2-fluoromethyl-3-methylsulphonyl-4-(4-methylphenyl)benzamide.

EXAMPLE 5

In analogy with Example 4, N-diaminomethylene-2-ethyl-3-aminosulphonyl-4-phenylbenzamide is obtained by reacting 1.0 g of 2-ethyl-3-aminosulphonyl-4-phenylbenzoic acid [obtainable by reacting methyl 2-ethyl-3-aminosulphonyl-4-bromobenzoate with phenylboronic acid in the presence of tetrakis(triphenylphosphine)-Pd(0) and then hydrolyzing] with 0.9 g of guanidinium chloride.

The following are obtained in an analogous manner from methyl 2-methyl-3-aminosulphonyl-4-(3-chlorophenyl)-benzoate, N-diaminomethylene-2-methyl-3-aminosulphonyl-4-(3-chlorophenyl)benzamide;
from 2-nitro-3-aminosulphonyl-4-(4-methoxyphenyl)-benzoic acid, N-diaminomethylene-2-nitro-3-aminosulphonyl)-4-(4-methoxyphenyl)benzamide;
from 2-cyano-3-aminosulphonyl-4-phenylbenzoic acid, N-diaminomethylene-2-cyano-3-aminosulphonyl-4-phenylbenzamide;
from 2-ethynyl-3-aminosulphonyl-4-(4-chlorophenyl)-benzoic acid, N-diaminomethylene-2-ethynyl-3-aminosulphonyl-4-(4-chlorophenyl)benzamide;

from 2-fluoro-3-aminosulphonyl-4-phenylbenzoic acid, N-diaminomethylene-2-fluoro-3-aminosulphonyl-4-phenylbenzamide;

from 2-difluoromethyl-3-aminosulphonyl-4-phenylbenzoic acid, N-diaminomethylene-2-difluoromethyl-3-aminosulphonyl-4-phenylbenzamide;

from 2-fluoromethyl-3-aminosulphonyl-4-(4-methylphenyl) benzoic acid, N-diaminomethylene-2-fluoromethyl-3-aminosulphonyl-4-(4-methylphenyl)benzamide.

EXAMPLE 6

In analogy with Example 1, N-diaminomethylene-2-methyl-4-(4-methylphenyl)-5-aminosulphonylbenzamide is obtained by reacting 1.8 g of methyl 2-methyl-4-(4-methylphenyl)-5-aminosulphonylbenzoate [obtainable by reacting methyl 3-aminosulphonyl-4-bromo-6-methylbenzoate with tolylboronic acid] with 1.5 g of guanidine in methanol.

The following are obtained in an analogous manner by reacting guanidine with methyl 2-ethyl-4-(4-methylphenyl)-5-aminosulphonylbenzoate, N-diaminomethylene-2-ethyl-4-(4-methylphenyl)-5-aminosulphonylbenzamide;
with methyl 2-propyl-4-(4-methylphenyl)-5-aminosulphonylbenzoate, N-diaminomethylene-2-propyl-4-(4-methylphenyl)-5-aminosulphonylbenzamide;
with methyl 2-isopropyl-4-(4-methylphenyl)-5-aminosulphonylbenzoate, N-diaminomethylene-2-isopropyl-4-(4-methylphenyl)-5-aminosulphonylbenzamide;
with methyl 2-butyl-4-(4-methylphenyl)-5-aminosulphonylbenzoate, N-diaminomethylene-2-butyl-4-(4-methylphenyl)-5-aminosulphonylbenzamide;
with methyl 2-(2-butyl)-4-(4-methylphenyl)-5-aminosulphonylbenzoate, N-diaminomethylene-2-(2-butyl)-4-(4-methylphenyl)-5-aminosulphonylbenzamide;
with methyl 2-ethyl-4-phenyl-5-aminosulphonylbenzoate, N-diaminomethylene-2-ethyl-4-phenyl-5-aminosulphonylbenzamide;
with methyl 2-propyl-4-phenyl-5-aminosulphonylbenzoate, N-diaminomethylene-2-propyl-4-phenyl-5-aminosulphonylbenzamide;
with methyl 2-isopropyl-4-phenyl-5-aminosulphonylbenzoate, N-diaminomethylene-2-isopropyl-4-phenyl-5-aminosulphonylbenzamide;
with methyl 2-butyl-4-phenyl-5-aminosulphonylbenzoate, N-diaminomethylene-2-butyl-4-phenyl-5-aminosulphonylbenzamide;
with methyl 2-(2-butyl)-4-phenyl-5-aminosulphonylbenzoate, N-diaminomethylene-2-(2-butyl)-4-phenyl-5-aminosulphonylbenzamide;
with methyl 2-ethyl-4-(4-methylphenyl)-5-aminosulphonylbenzoate, N-diaminomethylene-2-ethyl-4-(4-methylphenyl)-5-aminosulphonylbenzamide;
with methyl 2-chloro-4-(4-methylphenyl)-5-aminosulphonylbenzoate, N-diaminomethylene-2-chloro-4-(4-methylphenyl)-5-aminosulphonylbenzamide;
with methyl 2-bromo-4-(4-methylphenyl)-5-aminosulphonylbenzoate, N-diaminomethylene-2-bromo-4-(4-methylphenyl)-5-aminosulphonylbenzamide;
with methyl 2-fluoromethyl-4-(4-methylphenyl)-5-aminosulphonylbenzoate, N-diaminomethylene-2-fluoromethyl-4-(4-methylphenyl)-5-aminosulphonylbenzamide;
with methyl 2-trifluoromethyl-4-(4-methylphenyl)-5-aminosulphonylbenzoate, N-diaminomethylene-2-trifluoromethyl-4-(4-methylphenyl)-5-aminosulphonylbenzamide;
with methyl 2-pentafluoroethyl-4-(4-methylphenyl)-5-aminosulphonylbenzoate, N-diaminomethylene-2-pentafluoroethyl-4-(4-methylphenyl)-5-aminosulphonylbenzamide;
with methyl 2-methoxy-4-(4-methylphenyl)-5-aminosulphonylbenzoate, N-diaminomethylene-2-methoxy-4-(4-methylphenyl)-5-aminosulphonylbenzamide;
with methyl 2-cyano-4-(4-methylphenyl)-5-aminosulphonylbenzoate, N-diaminomethylene-2-cyano-4-(4-methylphenyl)-5-aminosulphonylbenzamide;
with methyl 2-nitro-4-(4-methylphenyl)-5-aminosulphonylbenzoate, N-diaminomethylene-2-nitro-4-(4-methylphenyl)-5-aminosulphonylbenzamide;
with methyl 2-ethynyl-4-(4-methylphenyl)-5-aminosulphonylbenzoate, N-diaminomethylene-2-ethynyl-4-(4-methylphenyl)-5-aminosulphonylbenzamide.

EXAMPLE 7

In analogy to Example 1 the following are obtained by reacting guanidine with methyl 2-trifluoro-5-phenylbenzoate: N-diaminomethylene-2-trifluoro-5-phenylbenzamide;
with methyl 2-bromo-5-phenylbenzoate: N-diaminomethylene-2-bromo-5-phenylbenzamide;
with methyl 2-methyl-5-phenylbenoate: N-diaminomethylene-2-methyl-5-phenylbenzamide;
with methyl 2-methyl-5-(4-methylphenyl)-benzoate: N-diaminomethylene-2-methyl-5-(4-methylphenyl)-benzamide.

The examples which follow relate to pharmaceutical preparations:

Example A: Injection Vials

A solution of 100 g of an active compound of the formula I and 5 g of disodium hydrogen phosphate in 3 l of double-distilled water is adjusted to pH 6.5 using 2N hydrochloric acid, sterilized by filtration and used to fill injection vials; the solution in the vials is then lyophilized under sterile conditions and the vials are then sealed in a sterile manner. Each injection vial contains 5 mg of active compound.

Example B: Suppositories

A mixture of 20 g of an active compound of the formula I is melted together with 100 g of soyabean lecithin and 1400 g of cocoa butter and the mixture is poured into moulds and allowed to cool. Each suppository contains 20 mg of active compound.

Example C: Solution

A solution is prepared consisting of 1 g of an active compound of the formula I, 9.38 g of $NaH_2PO_4.2\ H_2O$, 28.48 g of $Na_2HPO_4.12\ H_2O$ and 0.1 g of benzalkonium chloride in 940 ml of double-distilled water. The solution is adjusted to pH 6.8, made up to 1 l and sterilized by irradiation. This solution can be used in the form of eye drops, for example.

Example D: Ointment 500 mg of an active compound of the formula I are mixed with 99.5 g of vaseline under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed, in a customary manner, into tablets such that each tablet contains 10 mg of active compound.

Example F: Coated tablets

Tablets are compressed in analogy with Example E, which tablets are subsequently coated, in a customary manner, with a coating consisting of sucrose, potato starch, talc, gum tragacanth and colouring matter.

Example G: Capsules

Hard gelatine capsules are filled, in a customary manner, with 2 kg of active compound of the formula I such that each capsule contains 20 mg of the active compound.

Example H: Ampoules

A solution of 1 kg of active compound of the formula I in 60 l of double-distilled water is sterilized by filtration and used to fill ampoules; the solution in the ampoules is lyophilized under sterile conditions and the ampoules are sealed in a sterile manner. Each ampoule contains 10 mg of active compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. Arylbenzoylguanidines of the formula I

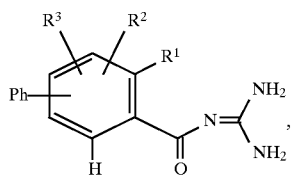

in which $R^1$ is A, $R^2$ and $R^3$ are, in each case independently of each other, H, $-SO_n-R^6$ or $-SO_2NR^4R^5$, $R^4$ is H, A, cycloalkyl having from 5 to 7 C atoms, cycloalkylmethyl having from 6 to 8 C atoms, $CF_3$, $CH_2F$, $CHF_2$, $CH_2CF_3$, Ph or $-CH_2$-Ph, $R^5$ is H or A, or else $R^4$ and $R^5$ are together also alkylene having from 4 to 5 C atoms, where one $CH_2$ group can also be replaced by O, S, NH, N-A or $N-CH_2$-Ph, $R^6$ is A or Ph, A is alkyl having from 1 to 6 C atoms, Ph is phenyl, which is unsubstituted or is substituted once, twice or three times by A, OA, $NR^4R^5$, F, Cl, Br, I or $CF_3$, and n is 1 or 2, and the physiologically harmless salts thereof.

2. A compound selected from the group consisting of
(a) N-Diaminomethylene-2-methyl-4-(4-methylphenyl)-5-methylsulphonylbenzamide;
(b) N-Diaminomethylene-2-ethyl-4-(4-methylphenyl)-5-methylsulphonylbenzamide;
(c) N-Diaminomethylene-2-methyl-3-methylsulphonyl-4-(2-methylphenyl)benzamide;
(d) N-Diaminomethylene-2-ethyl-3-methylsulphonyl-4-phenylbenzamide.

3. Process for preparing arylbenzoylguanidine derivatives of the formula I according to claim 1, and also the salts thereof, characterized in that a compound of the formula II

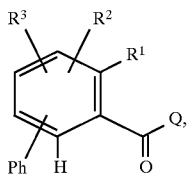

in which $R^1$, $R^2$, $R^3$ and Ph have the previously mentioned meanings, and

Q is Cl, Br, OA, O—CO-A, O—CO-Ph or OH, or another reactive, esterified OH group or leaving group which can readily be substituted nucleophilically, is reacted with guanidine, or in that a benzoylguanidine of the formula III

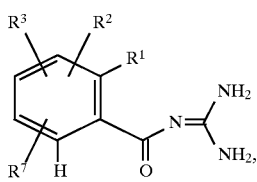

in which $R^1$, $R^2$ and $R^3$ have the previously mentioned meanings, and $R^7$ is Cl, Br, I or $O-SO_2-R^8$, and $R^8$ is A, Ph or $CF_3$, is reacted with a compound of the formula IV

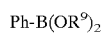

$$Ph-B(OR^9)_2 \qquad \text{IV}$$

in which $R^9$ is in each case H, A or, together, alkylene having from 2 to 4 C atoms, or in that a compound which contains one or more reducible group(s) and/or one or more additional C—C and/or C—N bond(s) in place of one or more hydrogen atoms, but which otherwise conforms to the formula I, is treated with a reducing agent, or in that a compound which contains one or more solvolysable group(s) in place of one or more hydrogen atoms, but which otherwise conforms to the formula I, is treated with a solvolysing agent, and/or in that a base of the formula I which has been obtained is converted into one of its salts by being treated with an acid.

4. Process for producing pharmaceutical preparations, which comprises bringing a compound of the formula I according to claim 1 or one of its physiologically harmless salts, together with at least one solid, liquid or semiliquid carrier substance or auxiliary substance, into a suitable dosage form.

5. Pharmaceutical preparation, comprising
at least one compound of the general formula I according to claim 1 or one of its physiologically harmless salts.

6. A method of providing cardioprotection, by the inhibition of cellular Na+/H exchange system, to an individual in need thereof, said method comprising administering an effective amount of a compound of formula I as defined in claim 1.

7. A method according to claim 6 for the treatment of arrhythmias, angina pectoris and infarctions.

* * * * *